United States Patent [19]

Gertisser et al.

[11] 4,244,872
[45] Jan. 13, 1981

[54] COUMARIN DYESTUFFS

[75] Inventors: Berthold Gertisser, Münchenstein; Beat Henzi, Neuallschwil, both of Switzerland

[73] Assignee: Sandoz Ltd., Basle, Switzerland

[21] Appl. No.: 953,562

[22] Filed: Oct. 23, 1978

Related U.S. Application Data

[63] Continuation-in-part of Ser. No. 591,602, Jun. 30, 1975, abandoned.

[30] Foreign Application Priority Data

Jul. 3, 1974 [CH] Switzerland ............... 9103/74

[51] Int. Cl.³ .................................... C07D 311/16
[52] U.S. Cl. ...................................... 260/343.45
[58] Field of Search .............................. 260/343.4 S

[56] References Cited

U.S. PATENT DOCUMENTS 3,985,772  10/1976  Scheuermann et al. ...... 260/343.4 S

*Primary Examiner*—Henry R. Jiles
*Assistant Examiner*—R. W. Ramsuer
*Attorney, Agent, or Firm*—Gerald D. Sharkin; Richard E. Vila; Thomas C. Doyle

[57] ABSTRACT

Disclosed are cationic dyestuffs being coumarin or coumarinimide derivatives free from sulpho groups, bearing a 7-amino group and being characterized by having, in the 3-position, a cationic group of formula (a),

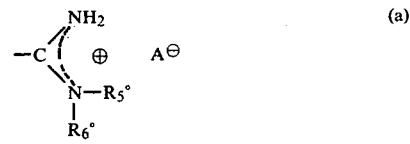

in which
$A^\ominus$ signifies an anion,
either
  $R_5°$ signifies hydrogen or optionally substituted alkyl or cycloalkyl, and
  $R_6°$ signifies hydrogen, or optionally substituted alkyl or cycloalkyl, or, where $R_5°$ is hydrogen, also hydroxy, naphthyl, optionally substituted amino or alkoxy, or phenyl monosubstituted by phenoxy, chlorophenoxy,
  benzyl, amino or $C_1$-$C_4$ alkylamino,
or
  $R_5°$ and $R_6°$, together with the nitrogen to which they are attached, signify a non-aromatic heterocycle,
  and the dotted line indicates that the positive charge is not localized, their production and use for dyeing and printing basic dyeable substrates, plastics and paper, particularly acid modified polyester substrates. They give dyeings of yellow to greenish yellow which fluoresce in the yellow to greenish yellow band.

9 Claims, No Drawings

COUMARIN DYESTUFFS

This application is a continuation-in-part of copending application Ser. No. 591,602 filed June 30, 1975 and now abandoned.

The invention relates to cationic dyestuffs of the coumarin or coumarinimide type.

According to the invention there are provided cationic dyestuffs being coumarin or coumarinimide derivatives free from sulpho groups, bearing a 7-amino group and being characterised by having, in the 3-position, a cationic group of formula (a)

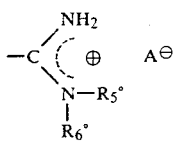

in which
$A^{\ominus}$ signifies an anion,
either $R_5°$ signifies hydrogen or optionally substituted alkyl or cycloalkyl, and $R_6°$ signifies hydrogen, or optionally substituted alkyl or cycloalkyl, or, where $R_5°$ is hydrogen, also hydroxy, naphthyl, optionally substituted amino or alkoxy, or phenyl monosubstituted by phenoxy, chlorophenoxy, benzyl, amino or $C_1$–$C_4$ alkylamino,
or $R_5°$ and $R_6°$, together with the nitrogen to which they are attached, signify a non-aromatic heterocycle, and the dotted line indicates that the positive charge is not localised.

The coumarin or coumarinimide nucleus, the amino group in the 7-position, and the optionally substituted groups as $R_5°$ and $R_6°$ may bear such substituents as do not deleteriously affect the dyeing properties of the compounds. For example, the 4-position of the nucleus may be substituted by an optionally substituted alkyl radical and the 7-amino group may be primary, secondary, tertiary or cyclic, the secondary amino group bearing, for example, an optionally substituted alkyl, cyclohexyl, phenyl or naphthyl radical, the tertiary amino group bearing, for example, two optionally substituted alkyl radicals, the cyclic amino group being non-aromatic, optionally substituted and optionally containing a further hetero atom. The 6-position of the nucleus may, for example, be substituted by halogen or by an optionally substituted alkyl or may be linked through a bridging group with the N atom of the 7-amino group so as to form a heterocyclic ring.

Preferred radicals of formula (a) are the radicals of formula (a'),

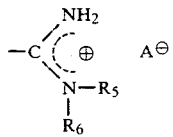

in which
$A^{\ominus}$ is as defined above,
either
$R_5$ is hydrogen; $C_{1-6}$ alkyl, unsubstituted or monosubstituted by hydroxy, phenyl, phenoxy or $C_{1-4}$ alkoxy; or cyclohexyl, unsubstituted or substituted by up to three $C_{1-4}$ alkyls, and $R_6$ is hydrogen; $C_{1-6}$ alkyl; cyclopentyl; or cyclohexyl unsubstituted or substituted by up to three $C_{1-4}$ alkyls; or, where $R_5$ is hydrogen, also hydroxy; $C_{1-4}$ alkoxy; amino; mono- or di-$(C_{1-4})$ alkylamino; phenylamino; benzylamino; morpholino; pyrrolidino; naphthyl; or phenyl monosubstituted by phenoxy, monochlorophenoxy, amino, mono$(C_{1-4})$ alkylamino or benzyl, or
$R_5$ and $R_6$, together with the nitrogen to which they are attached, form a 5 or 6-membered non-aromatic heterocycle optionally containing a further hetero atom, e.g. a morpholine, piperazine or piperidine ring.

Preferred significances of $R_5$, when not joined with $R_6$ to form a heterocycle, are hydrogen, $C_{1-4}$ alkyl, 3-$(C_{1-4})$alkoxypropyl, 2-hydroxyethyl, 2-hydroxypropyl, phenylethyl and cyclohexyl, more preferably hydrogen, $C_{1-4}$ alkyl, 3-$(C_{1-4})$alkoxypropyl and cyclohexyl, still more preferably hydrogen, methyl, ethyl, propyl, butyl, cyclohexyl and 3-methoxypropyl, and most preferably hydrogen.

Preferred significances of $R_6$, when not joined with $R_5$, are hydrogen, $C_{1-4}$ alkyl or cyclohexyl, or, where $R_5$ is hydrogen, also hydroxy, 1-naphthyl, amino, mono- or di-$(C_{1-2})$ alkylamino, phenylamino, benzylamino, morpholino, pyrrolidino or phenyl monosubstituted by phenoxy, benzyl or amino, more preferably hydrogen, $C_{1-4}$ alkyl or cyclohexyl, or, where $R_5$ is hydrogen, also amino, phenylamino, dimethylamino, morpholino, pyrrolidino, hydroxy or phenyl monosubstituted by phenoxy, benzyl or amino, still more preferably hydrogen, methyl, ethyl, propyl or cyclohexyl, or where $R_5$ is hydrogen, also amino, dimethylamino or hydroxy. Most preferably $R_6$ is hydrogen.

Representative of the compounds provided by the invention are the compounds of formula I,

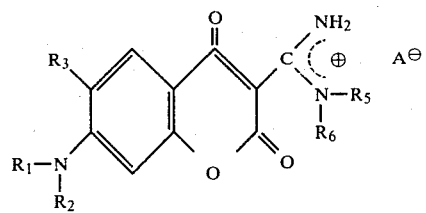

in which
$R_5$ and $R_6$ and their preferred significances are as defined above,
$A^{\ominus}$ is as defined above,
either,
(1) $R_1$ is hydrogen; phenyl; cyclohexyl; $C_{1-6}$ alkyl, unsubstituted or substituted by up to two halogens or by a hydroxy, cyano, $C_{1-4}$ alkoxy, phenyl, phenoxy, benzoyloxy, benzyloxy, carboxamide, $(C_{1-4})$alkoxycarbonyl or benzoyl; or a radical (f),

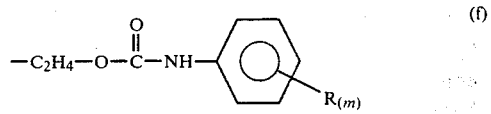

where
R is halogen, $C_{1-4}$ alkyl or alkoxy and m is 0, 1 or 2, and (1a) $R_2$ is hydrogen; $C_{1-6}$ alkyl unsubstituted or substituted by up to two halogens or by a hydroxy, cyano, $C_{1-4}$ alkoxy, phenyl, phenoxy, $(C_{1-4})$ alkoxycarbonyl, benzyloxy, carboxamido or benzoyloxy; or a radical (f), above, and $R_3$ is hydrogen, halogen or $C_{1-4}$ alkyl or (1b) $R_2$ together with $R_3$ signifies a bridge radical of formula (g) to (k)

$$-CH_2-CH_2-CH_2-, \quad -CH_2-CH_2-, \quad -\underset{\underset{CH_3}{|}}{CH}-CH_3,$$

(g)          (h)          (i)

$$-\underset{\underset{CH_3}{|}}{CH}-\underset{\underset{CH_3}{|}}{\overset{\overset{CH_3}{|}}{C}}-, \quad \text{or} \quad -\underset{\underset{CH_3}{|}}{\overset{\overset{CH_3}{|}}{C}}-CH_2-\underset{\underset{CH_3}{|}}{CH}-$$

(j)               (k)

or (2) $R_1$ and $R_2$, together with the nitrogen, form a 5 or 6 membered non-aromatic ring which optionally contains a further hetero atom, preferably morpholine, pyrrolidine, piperazine or piperidine, more preferably morpholine or piperidine, and $R_3$ is hydrogen, halogen or $C_{1-4}$ alkyl, and $R_4$ is hydrogen, benzyl or $C_{1-4}$ alkyl.

Where any alkyl as $R_1$ or $R_2$ is substituted by hydroxy, cyano, phenoxy or $C_{1-4}$ alkoxy, such alkyl is preferably of two carbon atoms, when substituted by benzyloxy, such alkyl is preferably of two or three carbon atoms and when substituted by phenyl, such alkyl is preferably methyl, i.e. forming a benzyl radical.

$R_1$, when not forming a heterocycle with $R_2$, is preferably $C_{1-4}$ alkyl, cyclohexyl, benzyl, 2-phenoxy-, 2($C_{1-4}$)alkoxy-, 2-cyano-, 2-hydroxy-, 2-phenylcarbamoyloxy- or 2-benzyloxy-ethyl, 2-benzyloxypropyl or 3-benzyloxypropyl, more preferably $C_{1-4}$ alkyl, cyclohexyl or 2-benzyloxyethyl, most preferably methyl or ethyl.

$R_2$, when not forming a heterocycle with $R_1$ or a bridge with $R_3$, is preferably $C_{1-4}$ alkyl (preferably methyl or ethyl), benzyl or 2-benzyloxyethyl, more preferably $C_{1-4}$ alkyl or 2-benzyloxyethyl, most preferably methyl or ethyl.

Where $R_1$ and $R_2$ together form a heterocycle, the preferred and more preferred heterocycles are as given above in formula I.

$R_3$, when not forming a bridge with $R_2$, is preferably hydrogen. When $R_2$ and $R_3$ form a bridge, such is preferably of formula (i), (j) or (k), above. $R_4$ is preferably hydrogen.

As a preferred class of compounds may be given the compounds of formula I', where $A^{\ominus}$ is as defined above, either (1) $R_1'$ is $C_{1-4}$ alkyl, cyclohexyl, benzyl, 2-phenoxy-, 2-$(C_{1-4})$ alkoxy-, 2-cyano-, 2-hydroxy-, 2-phenylcarbamoyloxy- or 2-benzyloxy-ethyl, or 2- or 3-benzyloxypropyl, and (1a) $R_2'$ is $C_{1-4}$ alkyl, benzyl or 2-benzyloxyethyl, and $R_3'$ is hydrogen or (1b) $R_2'$ and $R_3'$, together form a bridge radical (i), (j) or (k) above (2) $R_1'$ and $R_2'$, together with the nitrogen, form a morpholine or piperidine ring, $R_3'$ is hydrogen, or either $R_5'$ is hydrogen, $C_{1-4}$ alkyl, 3-$(C_{1-4})$alkoxypropyl, 2-hydroxyethyl, 2-hydroxypropyl, phenylethyl or cyclohexyl, and $R_6'$ is hydrogen, $C_{1-4}$ alkyl or cyclohexyl, or, where $R_5'$ is hydrogen, also hydroxy, 1-naphthyl, amino, mono- or di-$C_{1-2}$ alkylamino; phenylamino, benzylamino, N-morpholino, N-pyrrolidino, or phenyl monosubstituted by phenoxy, benzyl or amino, or $R_5'$ and $R_6'$, together with the nitrogen, form a morpholino, piperazino or piperidino ring.

Further preferred compounds are the compounds of formula I", where $A^{\ominus}$ is as defined above, $R_1''$ is $C_{1-4}$ alkyl, 2-benzyloxyethyl or cyclohexyl, $R_2''$ is $C_{1-4}$ alkyl or 2-benzyloxyethyl, $R_5''$ is hydrogen, $C_{1-4}$ alkyl, 3-$(C_{1-4})$alkoxypropyl or cyclohexyl, and $R_6''$ is hydrogen; cyclohexyl; or $C_{1-4}$ alkyl; or, when $R_5''$ is hydrogen, also amino; phenylamino; dimethylamino; hydroxy; phenyl mono-substituted by phenoxy, benzyl or amino; N-morpholino or N-pyrrolidino, particularly the compounds of formula I''',

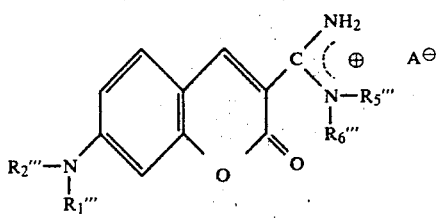

where
A⊖ is as defined above,
R₁''' and R₂''', independently, are methyl or ethyl,
R₅''' is hydrogen, methyl, ethyl, propyl, butyl, cyclohexyl or 3-methoxypropyl,
R₆''' is hydrogen, methyl, ethyl, propyl or cyclohexyl, or, where R₅'' is hydrogen, also amino, dimethylamino or hydroxy.

Of particular interest are the compounds of formula I''' in which R₅''' and R₆'' are both hydrogen.

By halogen, as used herein, is to be understood bromine, fluorine, iodine or chlorine, chlorine being the preferred halogen.

The exact nature of the anion A⊖ is not critical, and may be any of the anions conventional in the cationic dyestuff art, preferably being nonchromophoric. As suitable examples may be given the chloride, bromide, sulphate, bisulphate, methylsulphate, aminosulphate, perchlorate, benzenesulphonate, oxalate, maleinate, acetate, propionate, lactate, succinate, tartrate, malate, methanesulphonate and benzoate anions as well as complex anions such as ZnCl₃⊖.

The compounds of the invention may, for example, be obtained by reacting an aniline derivative, substituted in the 3-position by hydroxy or alkoxy in the 4-position by an aldehyde or keto group and in the 6-position optionally by halogen or alkyl, with a compound of formula

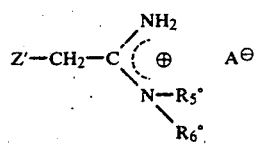

where
Z' is

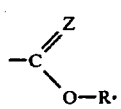

or —CN,
Z is O or NH,
R· is $C_{1-4}$ alkyl, and
A⊖, R₅° and R₆° are as defined above.

In particular, the compounds of formula I may be obtained by (a) reacting a compound of formula III,

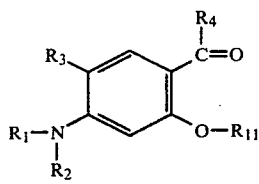

where
R₁, R₂, R₃ and R₄ are as defined above, and R₁₁ is hydrogen or $C_{1-4}$ alkyl,
with a compound of formula II',

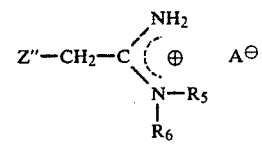

where
R₅, R₆ and A⊖ are as defined above,

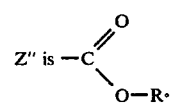

or —CN, and
R· is as defined above, or b), obtaining a compound of formula I, in which R₆ is other than naphthyl or substituted phenyl, by reacting a compound of formula III, above, with a compound of formula IV,

Z''—CH₂CN  IV where Z'' is as defined above,
and with a compound of formula V,

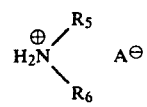

where R₅, R₆ and A⊖ are as defined above.

The process involving reaction with the compound II, and in particular process a), is suitably carried out in organic media, e.g. in low molecular alcohols and ketones, in particular in mono or polyhydric alkanols or ether alkanols, such as methanol, ethanol, propanol, butanol, cellosolve, methyl cellosolve and tetrahydrofuran.

The reaction is suitably carried out at from room temperature to 150° C., preferably from 60° to 80° C. The reaction is preferably base catalysed, e.g. using organic bases such as primary, secondary and tertiary amines, e.g. using piperidine or morpholine.

Process b) is suitably carried out under similar conditions to those above described. Where, in the compound V, A⊖ is a weak anion, e.g. an acetate or propionate anion, the reaction may be carried out without catalyst. However, if A⊖ is a strong anion, such as the chloride anion, then base catalysis, e.g. employing piperidine, is preferably employed.

If desired, the particular anion A⊖ obtained by the above processes may be exchanged for another in conventional manner, e.g. using an ion exchanger.

The resulting compounds of the invention may be isolated and purified in conventional manner.

The starting materials in the above processes are either known or may be obtained in conventional manner from available starting materials.

The compounds of the invention are cationic dyestuffs and may be employed for the dyeing and printing of basic dyeable substrates, in particular substrates comprising or consisting of homo- or mixed polymers of acrylonitrile, asymmetrical dicyanoethylene, and acid modified polyamide and polyester. They may also be employed for dyeing plastics in the mass and leather.

The polymeric substrates are, for example, textile substrates which may, for example, be in fibre, thread, woven or non-woven form. The acid modified polyamides may, for example, be those described in Belgian Pat. No. 706,104 and the acid modified polyesters those, for example, described in U.S. Pat. No. 3,379,723.

The dyeing or printing may be effected in conventional manner. For example, textile substrates may be dyed from an aqueous, neutral or acid medium at from 60° to the boiling temperature, optionally under superatmospheric pressure.

If desired, the compounds of the invention may be converted into dyeing preparations, for example into stable, liquid or solid dyeing preparations, e.g. by grinding or granulation or dissolving in appropriate solvents, optionally employing such adjuvants as stabilizers and solvent aids such as urea. Such preparations may, for example, be obtained as described in French Pat. Nos. 1,572,030 and 1,581,900.

The dyeings obtained are fluoroescent yellowish to greenish-yellow and possess, particularly when obtained using the preferred compounds, notable light and wet fastness and notable fastness to washing, perspiration, sublimation, pleating, decatizing, ironing, sea-water, dry-cleaning, cross-dyeing and solvents. The compounds show notable salt stability and solubility properties, particularly in water and organic solvents. The solubility in organic solvents enables their use in the dyeing of natural or synthetic plastics and resins in the mass.

The compounds also exhaust well from weakly acid dyebaths and exhibit good build-up on basic-dyeable substrates, for example polyacrylonitrile.

The compounds of the invention may be employed in dyeing or printing either singly or in admixture one with another or in the admixture with other cationic dyes.

The following Examples, in which all parts and percentages are by weight and the temperatures in degrees Centigrade, illustrate the invention.

EXAMPLE 1

98.6 Parts of 4-diethylamino salicylic aldehyde and 56.5 parts of cyano ethylacetate are completely dissolved in 200 parts of ethanol at 60°. 38.5 Parts of anhydrous ammonium acetate are added to the solution. After 5 minutes a deep yellow precipitate begins to form. Precipitation is completed by boiling under reflux over the course of 15 minutes. The mixture is cooled to room temperature and filtered. The residue is washed with ethanol. 3 litres of water at 60° are subsequently added to the filter residue which is then stirred for 1 hour. The mixture is filtered clear and the dye of formula

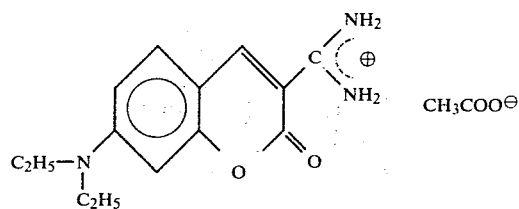

may be isolated by evaporating the aqueous solution in the form of the acetate or by salting out with sodium chloride in the form of the chloride which still contains a small amount of common salt as accompanying substance. On polyester fibres, modified by anionic groups, the dye provides fast greenish yellow shades with yellow to greenish fluorescence. Light and wet fastnesses are good.

Application Example A

20 Parts of the dye described in Example 1 and 80 parts of dextrin are ground in a pulverizing mill for 4 hours. The same dye mixture may also be obtained by pasting in 100 parts of water and subsequent atomizer drying. 1 Part of the obtained preparation is pasted with 1 part of 40% acetic acid. 200 Parts of demineralized water are poured over the paste which is then boiled for a short time. The mixture is diluted with 7000 parts of demineralized water, 2 parts of glacial acetic acid are added and 100 parts of polyacrylonitrile are introduced into the bath at 60°. The material may be pretreated over the course of 10 to 15 minutes at 60° in a bath consisting of 8000 parts of water and 2 parts of glacial acetic acid. The mixture is heated to 98°-100° over the course of 30 minutes, boiled for 1½ hours and rinsed. A greenish yellow dyeing with yellow to greenish yellow fluorescence is obtained. Light fasteness and wet fastness are good.

10 Parts of the dye of Example 1 are dissolved in 60 parts of glacial acetic acid and 30 parts of water. A constant concentrated dye solution which contains approximately 10% of the dye and which may be used according to the above application example for the dyeing of polyacrylonitrile, is obtained.

Application Example B

20 Parts of the dye of Example 1 are mixed in a ball mill with 80 parts of dextrin over the course of 48 hours. 1 Part of the obtained preparation is pasted with 1 part of 40% acetic acid and 200 parts of dimineralized water are poured over the paste which is then boiled for a short time. Dyeing with this solution is effected as follows:

(a) The mixture is diluted with 7000 parts of demineralized water; 21 parts of calcined sodium sulphate, 14 parts of ammonium sulphate, 14 parts of formic acid and 15 parts of a carrier, based on reaction products of ethylene oxide with dichlorophenols, are added and 100 parts of acid modified polyester fabric are introduced into the bath at 60°. The material may be pretreated over the course of 10 to 15 minutes at 60° in a bath consisting of 8000 parts of water and 2 parts of glacial acetic acid.

The mixture is heated to 98°-100° over the course of 30 minutes, boiled for 1 hour and rinsed. A level greenish yellow dyeing with yellow to greenish yellow fluorescence and good wet fastness is obtained.

(b) The mixture is diluted with 3000 parts of demineralized water; 18 parts of calcined sodium sulphate, 6 parts of ammonium sulphate and 6 parts of formic acid are added and 100 parts of acid modified polyester fabric are introduced into the bath at 60°. The mixture is heated in a closed vessel to 110° over the course of 45 minutes. This temperature is kept for 1 hour. The mixture is subsequently cooled to 60° over the course of 25 minutes and the material to be dyed is rinsed. A level greenish yellow dyeing with yellow to greenish yellow fluorescence with good wet fastness is obtained.

(c) The process is effected as described in b) but the closed vessel is heated to 120° over the course of 1 hour.

EXAMPLE 2

8.3 Parts of the compound of formula

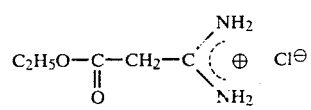

produced in accordance with known methods are dissolved at room temperature in 30 parts of ethyl alcohol containing 5 to 10% of water. 9.6 Parts of 4-dimethylamino-salicylic aldehyde are added to this solution and the resulting suspension is heated to 50°–55° until a homogenous solution is obtained. 2.1 Parts of piperidine are added to this solution and the mixture which rapidly becomes deep yellow is stirred at 50°–55° over the course of 12 hours.

The ethyl alcohol and the piperidine are evaporated under water jet vacuum and a yellow crystal paste is obtained which is recrystallized from water. The resulting dye is identical with the cloride form of Example 1.

EXAMPLE 3

5.9 Parts of n-propylamine are added dropwise to 6.0 parts of glacial acetic acid. When the reaction heat has decreased, 40 parts of ethyl alcohol, 19.3 parts of 4-diethylamino salicylic aldehyde and 11.3 parts of cyano-ethylacetate are added and the suspension is heated to 75°–78°, whereupon complete dissolution is obtained. The solution turns gradually into a deep yellow shade.

As soon as a thin layer chromatogramme indicates that the 4-diethylamino salicylic aldehyde has reacted completely, the ethyl alcohol is evaporated. The remaining melt is dissolved in 80 parts of water at 90°–100°. The aqueous solution is stirred together with 1 part of active carbon and filtered clear at 90°. To the yellow dyed filtrate 12 parts of common salt are gradually added and the dye of formula

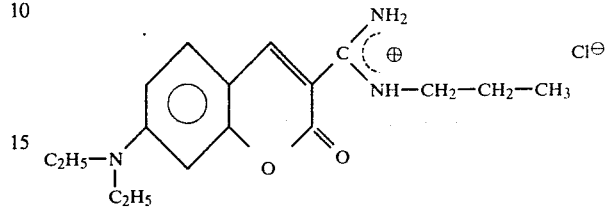

precipitates in crystalline form.

Applied on polyacrylonitrile fibres and basic dyeable polyester fibres the dye provides fast greenish yellow shades with yellow to greenish yellow fluorescence. Light fastness and wet fastness are good.

In the following Table I the structure of further dyes is indicated which may be produced in accordance with Examples 1 to 3. They correspond to formula

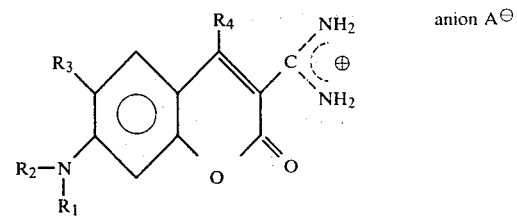

wherein $R_1$ to $R_4$ have the significances indicated in the columns.

Anions $A^\ominus$ may be those indicated in the description. Applied on polyester material, modified by anionic groups, the dyes give greenish yellow shades with yellow to greenish yellow fluorescence.

Table I

| Exp. No. | $R_1$ | $R_2$ | $R_3$ | $R_4$ |
|---|---|---|---|---|
| 4 | H | —CH$_3$ | H | H |
| 5 | H | —C$_2$H$_5$ | H | H |
| 6 | H | —CH$_2$—⌬ | H | H |
| 7 | —C$_2$H$_4$—CN | H | H | H |
| 8 | —C$_2$H$_4$—OCH$_3$ | H | H | H |
| 9 | —CH$_3$ | —CH$_3$ | H | H |
| 10 | " | —C$_2$H$_5$ | H | H |
| 11 | —C$_2$H$_4$—OH | —CH$_3$ | H | H |
| 12 | —C$_2$H$_4$—O—CH$_3$ | " | H | H |
| 13 | —C$_2$H$_4$—O—⌬ | " | H | H |
| 14 | —C$_2$H$_4$—O—CH$_2$—⌬ | " | H | H |

Table I-continued

| Exp. No. | R₁ | R₂ | R₃ | R₄ |
|---|---|---|---|---|
| 15 | —C₂H₄—O—C(=O)—NH—C₆H₅ | " | H | H |
| 16 | —C₂H₄—CN | " | H | H |
| 17 | —CH₂—CH(O—CH₂—C₆H₅)—CH₃ | " | H | H |
| 18 | —CH₂—CH₂—CH₂—O—CH₂—C₆H₅ | " | H | H |
| 19 | —C₂H₄—OH | —C₂H₅ | H | H |
| 20 | —C₂H₄—O—CH₃ | " | H | H |
| 21 | —C₂H₄—O—C₆H₅ | " | H | H |
| 22 | —C₂H₄—O—CH₂—C₆H₅ | " | H | H |
| 23 | —C₂H₄—O—C(=O)—NH—C₆H₅ | " | H | H |
| 24 | —C₂H₄—O—C(=O)—NH—C₆H₄—Cl | " | H | H |
| 25 | —C₂H₄—O—C(=O)—NH—C₆H₄—OCH₃ | " | H | H |
| 26 | —C₂H₄—CN | " | H | H |
| 27 | —CH₂—CH(O—CH₂—C₆H₅)—CH₃ | " | H | H |
| 28 | —CH₂—CH₂—CH₂—O—C(=O)—C₆H₅ | " | H | H |
| 29 | —C₂H₄—OH | —C₂H₄—OH | H | H |
| 30 | —C₂H₄—OCH₃ | —C₂H₄—O—CH₃ | H | H |
| 31 | —C₂H₄—O—CH₂—C₆H₅ | —C₂H₄—O—CH₂—C₆H₅ | H | H |
| 32 | —C₂H₄—CN | —C₂H₄—CN | H | H |
| 33 | —CH₂—CH(OH)—CH₃ | —CH₂—CH(OH)—CH₃ | H | H |
| 34 | —CH₂—CH₂—CH₂—OH | —CH₂—CH₂—CH₂—OH | H | H |
| 35 | —C₂H₄—O—C(=O)—NH—C₆H₅ | —C₂H₄—O—C(=O)—NH—C₆H₅ | H | H |
| 36 | —C₂H₅ | —C₂H₅ | —CH₃ | H |
| 37 | " | " | H | —CH₃ |
| 38 | " | " | H | —C₂H₅ |

Table I-continued

| Exp. No. | R₁ | R₂ | R₃ | R₄ |
|---|---|---|---|---|
| 39 | " | " | H | —CH₂—C₆H₅ |
| | R₁ together with R₂ | | | |
| 40 | —CH₂—(CH₂)₂—CH₂— | | H | " |
| 41 | —CH₂—(CH₂)₃—CH₂— | | H | " |
| 42 | H | R₂ together with R₃ —CH—C(CH₃)₂— with CH₃ | | " |
| 43 | —CH₃ | " | | " |
| 44 | —C₂H₅ | —CH—CH₂— with CH₃ | | " |
| 45 | H | —CH₂—CH₂—CH₂— | | " |
| 46 | —CH₃ | —C(CH₃)₂—CH₂—CH(CH₃)— | | H |
| 47 | —CH₂—CH₂—CH₃ | " | | H |
| 48 | —CH₂—C₆H₅ | " | | H |
| 49 | —CH₂—CH₂—C₆H₅ | " | | H |
| 50 | —CH₂—CH₂—O—C(O)—NH—C₆H₅ | " | | H |
| 51 | —CH₂—CH₂—OH | " | | H |
| 52 | —CH₂—CH₂—OCH₃ | " | | H |
| 53 | —CH₂—CH₂—O—CH₂—C₆H₅ | " | | H |
| 54 | —CH₃ | " | | —CH₃ |

In the following Table II the structure of further dyes is indicated which may be produced in accordance with Examples 1 to 3. They correspond to formula

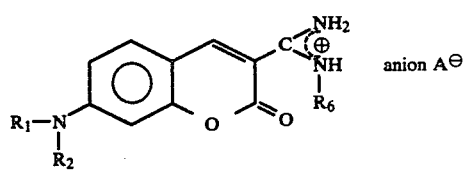

anion A⊖ wherein R₁, R₂ and R₆ have the significances indicated in the columns.
Anions A⊖ may be those indicated in the description.
Applied on polyester material, modified by anionic groups, the dyes give greenish yellow shades with yellow to greenish yellow fluorescence.

Table II

| Exp. No. | R₁ | R₂ | R₆ |
|---|---|---|---|
| 55 | —C₂H₅ | —C₂H₅ | —C₂H₅ |
| 56 | " | " | —C₆H₄—NH₂ |
| 57 | " | " | —C₄H₉ |
| 58 | " | " | C₆H₁₃ |
| 59 | " | " | (CH₃)₂—CH— |
| 60 | " | " | —(CH₂)₃—O—CH₃ |
| 61 | " | " | —C₆H₅ |
| 62 | " | " | NH₂ |
| 63 | " | " | —N(CH₃)₂ |
| 64 | " | " | morpholino (—N(CH₂CH₂)₂O) |
| 65 | " | " | —OH |
| 66 | " | " | —OCH₃ |
| 67 | " | " | —NH—C₆H₅ |
| 68 | " | " | —C₆H₄—O—C₆H₅ |
| 69 | " | " | naphthyl |
| 70 | —CH₃ | " | —C₂H₅ |
| 71 | " | " | —C₂H₄—OH |
| 72 | " | " | -n-C₄H₉ |

Table II-continued

| Exp. No. | R₁ | R₂ | R₆ |
|---|---|---|---|
| 73 | " | " | $-C_3H_6-O-CH_3$ |
| 74 | $-C_2H_5$ | $-C_2H_4CN$ | $-CH_3$ |
| 75 | " | " | $-C_2H_5$ |
| 76 | " | " | $-n-C_3H_7$ |
| 77 | " | " | $iso-C_3H_7$ |
| 78 | " | " | $-\overset{CH_3}{\underset{}{CH}}-CH_2-CH_3$ |
| 79 | " | " | $tert.-C_4H_9$ |
| 80 | " | " | tert. amyl |
| 81 | " | " | cyclohexyl |
| 82 | " | " | 3,3,5-trimethylcyclohexyl |
| 83 | " | " | cyclopentyl |
| 84 | " | " | $-NH_2$ |
| 85 | " | " | $-N(CH_3)_2$ |
| 86 | " | " | morpholino |
| 87 | " | " | piperidino |
| 88 | " | " | $-NH-\text{phenyl}$ |
| 89 | $-CH_3$ | $-CH_3$ | $-CH_3$ |
| 90 | " | " | $-C_3H_6-OCH_3$ |
| 91 | " | " | $-C_2H_5$ |
| 92 | " | " | cyclohexyl |
| 93 | " | " | cyclopentyl |
| 94 | " | " | $-NH_2$ |
| 95 | " | " | $-N(CH_3)_2$ |
| 96 | " | " | pyrrolidino |
| 97 | " | " | $-\text{C}_6\text{H}_4-CH_2-\text{C}_6\text{H}_5$ |
| 98 | " | " | $-NH-\text{phenyl}$ |
| 99 | " | " | $-N(CH_3)-\text{phenyl}$ |
| 100 | " | $-C_2H_4OH$ | $-CH_3$ |
| 101 | " | " | $-C_2H_5$ |
| 102 | " | " | $-C_2H_4-OH$ |
| 103 | " | " | $-C_3H_6-OCH_3$ |
| 104 | $-C_2H_5$ | $-CH_2-\overset{OH}{\underset{}{CH}}-CH_3$ | $-C_2H_5$ |
| 105 | cyclohexyl | H | $-CH_3$ |
| 106 | " | H | $-C_2H_5$ |
| 107 | " | H | $-C_3H_6-OCH_3$ |
| 108 | " | H | $iso-C_3H_7$ |
| 109 | " | H | $tert.-C_4H_9$ |
| 110 | " | H | $-NH_2$ |
| 111 | $-C_2H_5$ | $-C_2H_5$ | 1-methylnaphthyl |

In the following Table III the structure of further dyes is indicated which may be produced in accordance with Examples 1 to 3. They correspond to formula

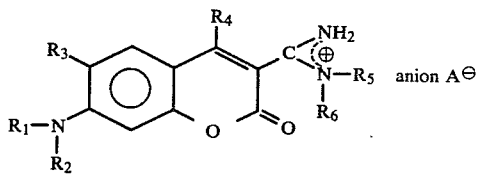

wherein $R_1$ to $R_6$ have the significances indicated in the columns.

Anions $A^\ominus$ may be those indicated in the description.
Applied on polyester material, modified by anionic groups, the dyes give greenish yellow shades with yellow to greenish yellow fluorescence.

Table III

| Exp. No. | R₁ | R₂ | R₃ | R₄ | R₅ | R₆ |
|---|---|---|---|---|---|---|
| 112 | $-C_2H_5$ | $-C_2H_5$ | H | H | $-C_2H_5$ | $-C_2H_5$ |
| 113 | " | " | H | H | $-C_3H_7$ | $-C_3H_7$ |
| 114 | " | " | H | H | $-CH_3$ | cyclohexyl |
| 115 | " | " | H | H | cyclohexyl | " |
| 116 | $-CH_3$ | " | H | $-CH_3$ | H | $-C_2H_5$ |
| 117 | $-C_2H_5$ | $-C_2H_4-CN$ | H | H | $-CH_3$ | $-CH_3$ |
| 118 | " | " | H | H | $-C_2H_5$ | $-C_2H_5$ |
| 119 | $-CH_3$ | $-CH_3$ | $-CH_3$ | H | H | $-CH_3$ |
| 120 | " | " | H | H | $-C_3H_6-O-CH_3$ | |
| 121 | " | " | H | H | $-CH_3$ | " |
| 122 | $-CH_3$ | $-CH_3$ | H | H | $-C_2H_5$ | $-C_2H_5$ |

Table III-continued

| Exp. No. | $R_1$ | $R_2$ | $R_3$ | $R_4$ | $R_5$ | $R_6$ |
|---|---|---|---|---|---|---|
| 123 | " | " | H | H | cyclohexyl-H | $-CH_3$ |
| 124 | " | $-C_2H_4-OH$ | H | H | $-CH_3$ | " |
| 125 | " | " | H | H | $-C_2H_5$ | $-C_2H_5$ |
| 126 | cyclohexyl-H | H | H | H | $-CH_3$ | $-CH_3$ |
| 127 | " | H | H | H | $-C_2H_5$ | $-C_2H_5$ |
| | | | | | $R_5$ together with $R_6$ | |
| 128 | $-C_2H_5$ | $-C_2H_5$ | H | H | $-CH_2-CH_2-O-CH_2-CH_2-$ | |
| 129 | " | " | H | H | $-CH_2-CH_2-CH_2-CH_2-CH_2-$ | |
| 130 | cyclohexyl-H | H | H | H | " | |
| 131 | " | H | H | H | $-CH_2-CH_2-CH_2-CH_2-$ | |
| | | | | | $R_5$ together with $R_6$ | |
| 132 | cyclohexyl-H | H | H | H | $-CH_2-CH_2-O-CH_2-CH_2-$ | |
| 133 | " | H | H | H | $-CH_2-CH_2-NH-CH_2-CH_2-$ | |
| 134 | $-CH_3$ | $-CH_3$ | H | H | $-CH_2-CH_2-CH_2-CH_2$ | |
| 135 | " | " | H | H | $-CH_2-CH_2-CH_2-CH_2-CH_2-$ | |
| 136 | " | " | H | H | $-CH_2-CH_2-O-CH_2-CH_2-$ | |
| 137 | " | " | H | H | $-CH_2-CH_2-NH-CH_2-CH_2-$ | |
| 138 | $-C_2H_5$ | $-C_2H_5$ | H | H | $-CH_2-CH_2-CH_2-CH_2-$ | |
| 139 | " | " | H | H | $-CH_2-CH_2-CH_2-CH_2-CH_2-$ | |
| 140 | " | " | H | H | $-CH_2-CH_2-O-CH_2-CH_2-$ | |
| 141 | " | " | H | H | $-CH_2-CH_2-NH-CH_2-CH_2-$ | |

What is claimed is:

1. A compound of formula I''',

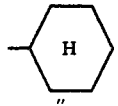

where
$A^\ominus$ is an anion,
$R_1'''$ and $R_2'''$, independently, are methyl or ethyl,
$R_5'''$ is hydrogen, methyl, ethyl, propyl, butyl, cyclohexyl or 3-methoxypropyl,
and the dotted line indicates that the positive charge is not localized.

2. A compound according to claim 1 wherein $R_5'''$ is hydrogen, methyl, ethyl, propyl, butyl or cyclohexyl.

3. A compound of claim 1, wherein $R_5'''$ signifies hydrogen.

4. A compound of claim 1, in which $R_5'''$ is other than hydrogen.

5. A compound of claim 1, of formula

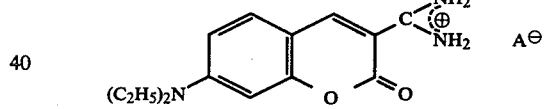

in which $A^\ominus$ is an anion.

6. A compound of claim 4, of formula

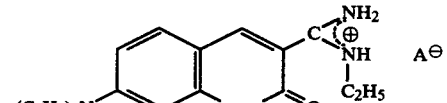

in which $A^\ominus$ is an anion.

7. A compound of claim 4, of formula

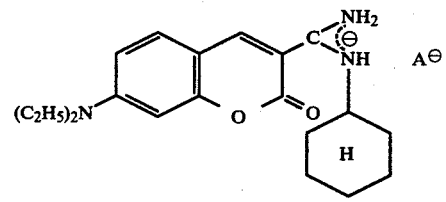

in which $A^\ominus$ is an anion.

8. The compound of claim 6 wherein $A^\ominus$ is the acetate ion.

9. The compound of claim 7 wherein $A^\ominus$ is the acetate ion.